United States Patent [19]

Derian et al.

[11] Patent Number: 5,556,628
[45] Date of Patent: Sep. 17, 1996

[54] FREE-FLOWING PSEUDOPLASTIC COSMETIC COMPOSITIONS/SUSPENSIONS

[75] Inventors: Paul-Jöel Derian, Fontenay-Aux-Roses; Claudie Willemin, Paris, both of France

[73] Assignee: Rhone-Poulenc Chimie, Courbevoie Cedex, France

[21] Appl. No.: 102,195

[22] Filed: Aug. 5, 1993

[30] Foreign Application Priority Data

Aug. 5, 1992 [FR] France ................................ 92 09692

[51] Int. Cl.$^6$ ...................................................... A61K 7/06
[52] U.S. Cl. .................... 424/401; 424/70.1; 424/70.19; 424/70.24; 514/880; 514/881; 514/937; 514/944
[58] Field of Search ...................................... 424/401, 489, 424/70, 70.1, 70.19, 70.24; 514/937, 944, 880, 881

[56] References Cited

U.S. PATENT DOCUMENTS 4,606,913  8/1986  Aronson et al. ...................... 424/59

FOREIGN PATENT DOCUMENTS

| 0043327 | 1/1982 | European Pat. Off. . |
| 0091331 | 10/1983 | European Pat. Off. . |
| 0210774 | 2/1987 | European Pat. Off. . |
| 0285389 | 10/1988 | European Pat. Off. . |
| 2188058 | 9/1989 | United Kingdom . |
| 9201507 | 2/1992 | WIPO . |

*Primary Examiner*—Jyothsna Venkat
*Attorney, Agent, or Firm*—Burns, Doane, Swecker & Mathis, L.L.P.

[57] ABSTRACT

Storage-stable, pseudoplastic free-flowing cosmetic compositions/formulations, for example shampoos, shower and exfoliating gels and hair lotions, comprise a stable and homogeneous suspension, in water, of water-insoluble particulates, and which further comprise at least one anionic surfactant, at least one nonionic or amphoteric cosurfactant and at least one electrolyte, these surfactants being present in such amounts as to impart pseudoplasticity thereto with a yield point of at least 0.2 Pa and constituting spherulites suspended within a lamellar phase.

15 Claims, No Drawings

FREE-FLOWING PSEUDOPLASTIC COSMETIC COMPOSITIONS/SUSPENSIONS

BACKGROUND OF THE INVENTION

1. Field of the Invention

The present invention relates to improved free-flowing cosmetic formulations comprising homogeneous and stabilized suspensions of water-insoluble particulates.

2. Description of the Prior Art

Typically in this art, formulations of cosmetic products of the shampoo, shower gel or make-up removing lotion types include a washing base, optionally a foaming agent, surface-active agents and various additives of the perfume or colorant type. Certain more sophisticated formulations also contain cosmetically/therapeutically active agents.

As long as these active agents/materials remain water-soluble, the preparation of the corresponding cosmetic, hair or body formulations does not present any problems. In contrast, the incorporation of water-insoluble active agents/materials presents problems of stability. It is essential to provide formulations which are homogeneous and which do not, during prolonged storage, sediment or phase separate.

In the current state of this art, one solution for avoiding this problem entails incorporating a thickener into the cosmetic formulation. Generally, this is a hydrocolloid such as xanthan gum, for example.

But including such thickening compounds does not always provide satisfactory results. In particular, the appearance of the corresponding cosmetic formulations may not satisfy cosmetic requirements. They generally exhibit a glairy or ropy appearance which is therefore unsuitable for a free, smooth and homogeneous flow which is particularly desirable to the user. Finally, hydrocolloids are expensive compounds which increase the cost of the formulations comprised thereof.

SUMMARY OF THE INVENTION

Accordingly, a major object of the present invention is the provision of improved cosmetic formulations comprising suspensions of water-insoluble particles, devoid of thickening agents of xanthan gum and other types and which do not display, in addition, a viscous behavior.

Briefly, the present invention features aqueous free-flowing cosmetic compositions containing water-insoluble particles in suspension, and further comprising at least one anionic surface-active agent, at least one cosurface-active agent of non-ionic or amphoteric type and at least one electrolyte, said surface-active agents or surfactants being present in amounts such that the compositions exhibit pseudoplastic behavior with a yield point equal to or greater than 0.2 Pa, as well as a lamellar phase structure confining spherulites which maintain said particles in suspension in a stable and homogeneous manner.

DETAILED DESCRIPTION OF PREFERRED EMBODIMENTS OF THE INVENTION

More particularly according to the present invention, it has now been determined that the combination of specific surface-active agents provides a medium possessing a rheological behavior which is unexpected, as it is surprisingly well suited, by virtue of its phase structure, for the suspension of the aforesaid particles or particulate material.

Suitable such anionic surface-active agents include, in particular, salts of fatty acids; alkali metal salts of mono- or dialkyl sulfates, mono- or dialkyl ether sulfates, lauryl ether sulfates, alkyl sulfonates, alkyl aryl sulfonates, alphaolefinsulfonates or alkyl phosphates, sulfonates of alkylphenolpolyglycol ethers; salts of alkyl sulfopolycarboxylic acid esters; salts of alkyl sulfosuccinates alkyl ether sulfosuccinates, alkyl isethionates or alkyl taurates; products of condensation of fatty acids with oxy- and aminoalkanesulfonic acids; sulfated derivatives of fatty acids and polyglycols; alkanolamides of sulfated fatty acids and salts of lipoamino acids. The lipoamino acids are prepared by acylation of the amino acids derived from the total hydrolysis of a natural protein. Particularly exemplary salts are the sodium, ammonium, magnesium and triethylamine salts.

In the case of sodium lauryl ether sulfate, LESNa, this is a surface-active agent widely used in shampoos by reason of its foaming properties. It is a cheap, conventional, washing base.

Exemplary of the non-ionic surface-active agents are, in particular, ethyoxylated fatty alcohols and especially those derived from lauryl, cetylstearyl, stearyl, cetyl and oleocetyl alcoholse Sucroglycerides can also be used.

Sucroglycerides are mixtures of compounds which are prepared by transesterification of natural or synthetic triglycerides with sucrose. These mixtures contain monoglycerides, diglycerides, small amounts of non-transesterified triglycerides, monoesters and diesters of sucrose.

EP-A-0,091,331 describes a process for preparing free-flowing sucroglycerides, and also indicates that such sucroglycerides have surface-active properties.

Exemplary of the amphoteric cosurface-active agents are those selected from among the betaines, such as oleylbetaine and sultaines of the cocoamidopropylhydroxysultaine type, and imidazoline derivatives such as cocoamphodiacetate.

These amphoteric compounds present, in addition, the advantage of constituting excellent washing bases which provide an abundant and stable washing foam. They are very safe for the human body and for the eyes.

Representative electrolytes include sodium or ammonium chloride.

Surprisingly, the combinations of the invention permit production of aqueous formulations having improved suspending properties and capable of maintaining solid or non-solid water-insoluble particles in suspension. Under the conditions of the invention, no sedimentation or separation whatsoever of the corresponding cosmetic compositions develops over time.

Preferably, the yield point of these compositions is equal to or greater than 0.2 Pa. For formulations based on mixtures of surface-active agents prepared at a temperature on the order of 50° C., this yield point has a value close to 1 Pa.

The corresponding cosmetic formulations exhibit a so-called lamellar phase structure comprising spherulites in suspension.

By "lameliar phase" is intended a hydrated solid phase or a liquid crystal phase in which several double layers are arranged in a parallel network, separated by layers of water or of an aqueous solution. In respect of the spherulites, these are multilamellar vesicles comprising several layers of surface-active agents arranged concentrically and generally ranging from 0.1 to 50 microns in size.

More specifically, the corresponding phase structure can be defined as that of a birefringent solution, optically characteristic of a non-isotropic mesomorphic phase.

By the term "water-insoluble particles" are intended solid or non-solid entities which are not solubilized in the aqueous medium of the subject composition. These, more particularly, are solid particles or emulsified droplets.

Representative solid particles include active materials or agents such as those used for hair treatments, e.g., zinc pyrithione, or any abrasive materials which may be of natural or synthetic origin. In particular, these are polycarbonates, polypropylenes, polyethylenes, alumina, calcite and clays. Such particles generally have a crystal size ranging from about 1 to 600 microns and preferably from about 10 to 400 microns.

In the case of the emulsified droplets, these are preferably droplets of at least one vegetable oil, essential oil and/or, more particularly, silicone oil.

The silicone oils which are well suited according to the present invention include the polyalkylsiloxanes, polyalkylarylsiloxanes and mixtures thereof. The preferred polyalkylsiloxanes are, especially, polydimethylsiloxanes such as dimethicone whose viscosity may range from about 20 Mpa.s to 50 Pa.s at 25° C., pure or mixed with cyclomethicone. Particularly exemplary of the polyalkylarylsiloxanes are the polyphenyldimethylsiloxanes.

In particular, polydiorganosiloxanes such as polydimethylsiloxanes having a molecular weight of less than or equal to 3,000,000 and polydimethyldiphenylsiloxanes of molecular weight of about 600,000 are especially well suited according to the invention.

The size of the oil droplets within the compositions of the invention advantageously ranges from about 0.5 to 50 microns.

The formulations according to the invention may contain approximately 0.5% to 8% and, preferably, about 1.5% to 4.5% by weight of water-insoluble particles.

Specific formulations of the invention include those:

(a) containing as anionic agent LESNa, as cosurface-active agent lauryl alcohol containing two moles of ethylene oxide and as electrolyte NaCl in a lauryl alcohol 2EO/LESNa mole ratio of from 2.1 to 4.3, (b) those containing as anionic agent a sodium lipoamino acid, the lipoproteol LC0® mixed with the same lauryl alcohol containing two ethoxy units and having a lauryl alcohol 2EO/sodium lipoamino acid mole ratio ranging from about 1.2 to 6.7, and (c) those containing as anionic agent LESNa, as cosurface-active agent oleylbetaine and as electrolyte NaCl, in an oleylbetaine/LESNa mole ratio of from 1.1 to 3.7.

Generally, the compositions according to the invention contain an anionic surface-active agent mixed with at least one cosurface-active agent in a cosurface-active agent/anionic surface-active agent mole ratio equal to or greater than 1.

The electrolyte used in these formulations is typically sodium chloride. The concentration thereof is adjusted to produce the desired formulation. Generally, it is greater than 10 g/l and preferably ranges from 10 to 40 g/l.

In a preferred embodiment of the invention, the subject compositions do not contain organic solvents, in particular hydrocarbon-based organic solvents, which, as described in GB-2,188,058, are used to suspend the solid particles.

All of the corresponding formulations are used to produce compositions according to the invention which are capable of maintaining water-insoluble particles in suspension during prolonged storage and which do not require the incorporation of any thickener.

Their content of washing base is less than 30%. They possess good wetting and foaming power, or strength. Finally, they have good skin and eye tolerance Of course, the compositions according to the invention may incorporate, in addition, other additives and adjuvants of the perfume, colorant and preservative type.

The compositions according to the invention may be provided either in the form of shampoos, shower gels, hair lotions or exfoliating gels.

The present invention also features a process for preparing the cosmetic compositions described above.

More specifically, such process comprises:

(i) mixing, with stirring and in aqueous medium, at least one anionic surface-active agent, at least one non-ionic and/or amphoteric cosurface-active agent and at least one electrolyte, said surface-active agents being present in such amounts that the resulting aqueous mixture has a pseudoplastic behavior with a yield point greater than or equal to 0.2 Pa and exhibits a lamellar phase structure enclosing spherulites, (ii) adding to said mixture the solid particles or at least one oil and, in the specific case of the oil, placing the resulting aqueous mixture under vigorous stirring such as to shear the oil into fine droplets inside the aqueous mixture, and (iii) recovering the cosmetic composition thus formulated.

The process according to the invention presents the advantage, on the one hand, of not requiring the prior preparation of a preformed aqueous emulsion of oil and, on the other hand, of preferably not employing organic solvents, in particular hydrocarbon-based organic solvents, which, per GB-2,188,058, are typically used to suspend the solid particles.

The oil emulsion is intrinsically formed inside the aqueous mixture. It is, in addition, stabilized therein immediately after its formation.

In order to further illustrate the present invention and the advantages thereof, the following specific examples are given, it being understood that same are intended only as illustrative and in nowise limitative.

EXAMPLE 1

Preparation of formulations suitable for stabilizing water-insoluble particles:

The formulations described below were prepared according to the following procedure:

The anionic surface-active agent was incorporated into salt water. The mixing was carried out with quite vigorous stirring using a frame-type blade at about 50° C. The cosurface-active agent was then gradually added and the mixture was maintained under stirring such as to obtain the expected phase structure which was monitored under a light or electron microscope.

1. Surface-active system A: an anionic surfactant and a non-ionic surfactant:

The anionic surfactant was a sodium lipoamino acid. It was, more particularly, lipoproteol LC0®, an aqueous solution of mixed salts of sodium and triethanolamine obtained by combining lauric acid with amino acids derived via the hydrolysis of collagen.

The non-ionic surfactant was ethoxylated lauryl alcohol containing 2 moles of ethylene oxide.

The electrolyte was an aqueous solution of sodium chloride, at a concentration of 16 g/l.

The formulations comprising this system of surface-active agents and which were suitable for stabilizing water-insoluble particles corresponded to a mole ratio value P of from 1.2 to 6.7, P designating the mole ratio of the molar percentage of non-ionic surface-active agent divided by the molar percentage value of anionic surface-active agent.

These formulations were characterized by a lamellar phase structure containing a suspension of spherulites. The size of the spherulites was determined under a light or electron microscope. It was on the order of 0.1 to 12 microns.

2. In a second anionic surface-active and non-ionic cosurface-active system B, LESNa was used in place of the lipoproteol LC0:

This was a 27% aqueous solution of sodium lauryl ether sulphate LESNa. For this system, the formulations corresponding to a spherulitic suspension in a lamellar phase were those having an ethyoxylated lauryl alcohol 2EO/LESNa mole ratio of 2.1 to 4.3.

3. Surface-active system: anionic surface-active agent/amphoteric cosurface-active agent:

The anionic surfactant was LESNa.

The amphoteric surfactant was a betaine, i.e., oleylbetaine. The electrolyte was a solution of sodium chloride, at a concentration of 40 g/l.

The corresponding formulations suitable for stabilizing solid particles, namely, which comprised a suspension of spherulites inside a lamellar phase, were determined for an oleylbetaine/LESNa molar ratio of from approximately 1.1 to 3.7.

Table I below sets forth three corresponding formulations:

TABLE I

| FORMULATION | A | B | C |
|---|---|---|---|
| LESNa | 5 | 5 | 4 |
| Oleylbetaine | 5.6 | 7.7 | 7.8 |
| Salt water | 88.4 | 86 | 86.8 |

Each of these three formulations was tested for its rheological properties by measuring its yield point and characterized by its viscoelastic properties.

(i) Yield point:

Measurements of the yield point were carried out on formulations A, B and C prepared at 50° C. using a Rheomat 30, Bingham model.

The results obtained are reported in Table II:

TABLE II

| Formulation | Yield (Pa) |
|---|---|
| A | 1.3 |
| B | 1.7 |
| C | 1.5 |

The high yield point values reflect good dispersing properties in the formulations A, B and C.

(ii) Measurement of viscoelastic properties during oscillation:

These were performed using a rheometric spectrometer RFS. The system was subjected to a sinusoidal deformation and the resulting torque was measured.

The G', G'', n* and Tan delta values were calculated from this measurement:

G'=modulus of elasticity,

G''=modulus of viscoelasticity, n* =complex viscoelasticity,

Tan delta =G''/G'.

For a given sample, the first operation was determining the amplitude of deformation below which G'' and G' remained constant when the measurement was prolonged. The frequency was set at 1 radian per second.

In a second stage, the deformation was set and the frequency was scanned, the deformation selected being situated at the level of the elasticity plateau.

For the three formulations selected, a viscoelastic behavior was recorded. For these three media, the modulus G' was greater than G'' over the entire range of frequencies of from 0.1 to 100 rad/se This result indicated that the solutions were elastic. On the other hand, they were pseudoplastic, since the apparent viscosity was a decreasing function of the frequency and the rate.

EXAMPLE 2

Formulations of cosmetic compositions according to the invention:

Anti-dandruff shampoos were prepared from the three formulations A, B and C. The corresponding shampoos are designated as V, W and Z. Thus, 2% of a 48% suspension of zinc pyrithione was introduced into each of the three formulations.

The corresponding shampoos were tested for the stability of their zinc pyrithione suspensions, for their foaming power and their wetting power.

(iv) Stability of the zinc pyrithione suspensions:

Regardless of the temperature, 20° C. or 40° C., the three shampoos were stable for more than three months.

(iv) Measurement of foaming power:

This was measured according to the AFNOR NFT 73404 standard used for surface-active agents. The technique included measuring the volume and the height of the foam formed at 30 seconds, 3 minutes and 5 minutes, respectively, after the end of flow.

The results obtained are reported in Table III:

TABLE III

| Formulation | 30 seconds ml | 3 minutes ml | 5 minutes ml |
|---|---|---|---|
| V | 390 | 395 | 370 |
| W | 365 | 355 | 350 |
| Z | 355 | 345 | 355 |

These results evidenced the good foaming power of the shampoos according to the invention.

(v) Measurement of wetting power:

This was measured according to the AFNOR NFT 73406 standard. This technique entailed determining the concentration in grams per liter of the solution of surface-active agent/distilled water sufficient to wet a cotton disc in 100 seconds at 20° C.

The wetting powers for LESNa and oleylbetaine are also reported in the following Table IV as control values:

TABLE IV

| Formulation | Wetting power g/l |
|---|---|
| LESNa | 2.10 |
| Oleylbetaine | 0.8 |
| V | 0.75 |
| W | 0.80 |
| Z | 0.85 |

Surprisingly, no decrease was observed in the wetting power of the formulations according to the invention incorporating LESNa, compared with the control formation containing only oleylbetaine. The association of oleylbetaine and LESNa unexpectedly permitted substantially increasing the wetting performance of LESNa.

(vi) Preparation of a specific shampoo formulation:

|  | % by weight |
| --- | --- |
| Sodium lauryl ether sulfate | 19.2 |
| Oleylbetaine | 18.8 |
| NaCl | 2.6 |
| Colorant | q.s |
| Rhodialux S ® | 0.05 |
| (UV-screening agent) | |
| Perfume | q.s |
| Zn PYRION ® (40%) | 2.4 |
| Water | q.s. 100 |

EXAMPLE 3

Preparation of a shampoo formulation incorporating, in suspension, droplets of an emulsified silicone oil:

|  | % by weight |
| --- | --- |
| Sodium lauryl ether sulfate | 26.92 |
| Oleylbetaine | 28.03 |
| SILBIONE 71631 ® | 3.33 |
| (30% solution of polydimethicone with a viscosity of 500,000 mPa.s in cyclomethicone) | |
| Colorant-preservative | q.s. |
| Perfume | 1.00 |
| NaCl | 1.74 |
| Deionized water | q.s. 100 |
| Citric acid | q.s. |

The above composition was prepared as follows:

Sodium lauryl ether sulfate was incorporated into salt water containing, in addition, a preservative. The mixing of the surface-active agent and the aqueous phase was carried out with fairly vigorous stirring using a frame-type blade at about 50° C. The oleylbetaine was in turn gradually added therein. The silicone oil, mixed with the perfume, was then introduced with very vigorous shearing. The shear rate was maintained for 5 to 10 minutes at 13,000 rpm (ultra-turrax)®. In this manner, the silicone oil was emulsified within the composition. The pH was then adjusted to 6 by adding citric acid. The viscosity of the final mixture was evaluated by measuring with a Brookfield viscosimeter. It was on the order of 11.3

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pseudoplastic free-flowing cosmetic composition comprising a stable and homogeneous suspension in water of water-insoluble particulates; the anionic surfactant sodium lauryl ether sulfate, a nonionic or amphoteric cosurfactant selected from the group consisting of a sucroglyceride, an ethoxylated fatty acid alcohol, a betaine, a sultaine, and an imadazoline compound; and an electrolyte; wherein said surfactant and cosurfactant are present in such amounts as to impart pseudoplasticity thereto with a yield point of at least 0.2 Pa and constituting spherulites suspended within a lamellar phase, and further wherein the suspension is in water devoid of organic solvent.

2. The cosmetic composition as defined by claim 1, wherein said electrolyte is sodium chloride or ammonium chloride.

3. The cosmetic composition as defined by claim 1, wherein said water-insoluble particulates are solid particles of zinc pyrithione, a natural abrasive, or a synthetic abrasive.

4. The cosmetic composition as defined by claim 1, wherein said water-soluble particulates are emulsified droplets of vegetable oil, essential oil, silicone oil, or a mixture thereof.

5. The cosmetic composition as defined by claim 1, said water-insoluble particulates comprising solids having a particle size of from about 1 to 600 microns.

6. The cosmetic composition as defined by claim 4, said emulsified droplets having a particle size of from about 0.5 to 50 microns.

7. The cosmetic composition as defined by claim 4, wherein said emulsified droplets are a polyalkylsiloxane, a polyalkylarylsiloxane, or mixture thereof.

8. The cosmetic composition as defined by claim 1, comprising from about 0.5% to 8% by weight of said water-insoluble particulates.

9. The cosmetic composition as defined by claim 1, comprising sodium lauryl ether sulfate, ethoxylated lauryl alcohol containing two moles of ethylene oxide and NaCl, in a lauryl alcohol to sodium lauryl ether sulfate mole ratio of from 2.1 to 4.3.

10. The cosmetic composition as defined by claim 1, comprising sodium lauryl ether sulfate, oleylbetaine and NaCl, in an oleylbetaine to sodium lauryl ether sulfate mole ratio of from 1.1 to 3.7.

11. The cosmetic composition as defined in claim 1, comprising a sodium lipoamino acid, and ethoxylated lauryl alcohol containing two ethoxy units, in a lauryl alcohol to sodium lipoamino acid mole ratio of from about 1.2 to 6.7.

12. The cosmetic composition as defined by claim 1, comprising a shampoo, a shower gel, a hair lotion, or an exfoliating gel.

13. The cosmetic composition as defined by claim 1, wherein said composition is devoid of hydrocolloid thickening agents.

14. A process for the formulation of the cosmetic composition as defined by claim 1, comprising intimately admixing into aqueous medium, under stirring, said anionic surfactant, said nonionic or amphoteric cosurfactant and said electrolyte, in such amounts as to impart said pseudoplasticity and spherulitic lamellar phase structure thereto, and then incorporating said water-insoluble particulates into the resulting stable and homogenous suspension.

15. A pseudoplastic free-flowing cosmetic composition comprising a stable and homogeneous suspension in water of water-insoluble emulsified droplets of oil, the anionic surfactant sodium lauryl ether sulfate, a nonionic or amphoteric cosurfactant selected from the group consisting of a sucroglyceride, an ethoxylated fatty acid alcohol, a betaine, a sultaine, and an imadazoline compound; and an electrolyte; wherein said surfactant and cosurfactant are present in such amounts as to impart pseudoplasticity thereto with a yield point of at least 0.2 Pa and constituting spherulites suspended within a lamellar phase, and further wherein the suspension is in water devoid of organic solvent.

* * * * *